US012606599B2

(12) United States Patent
Chen et al.

(10) Patent No.: US 12,606,599 B2
(45) Date of Patent: Apr. 21, 2026

(54) OVER-EXPRESSION OF GDS1 IN YEAST FOR INCREASED ETHANOL AND DECREASED ACETATE PRODUCTION

(71) Applicant: DANISCO US INC, Palo Alto, CA (US)

(72) Inventors: Zhongqiang Chen, Wilmington, DE (US); Min Qi, Palo Alto, CA (US); Luan Tao, Wallingford, PA (US); Quinn Qun Zhu, West Chester, PA (US)

(73) Assignee: DANISCO US INC., Palo Alto, CA (US)

( * ) Notice: Subject to any disclaimer, the term of this patent is extended or adjusted under 35 U.S.C. 154(b) by 492 days.

(21) Appl. No.: 18/170,454

(22) Filed: Feb. 16, 2023

(65) Prior Publication Data

US 2023/0331789 A1     Oct. 19, 2023

Related U.S. Application Data

(63) Continuation of application No. 17/281,068, filed as application No. PCT/US2019/053061 on Sep. 26, 2019, now abandoned.

(60) Provisional application No. 62/738,582, filed on Sep. 28, 2018.

(51) Int. Cl.
| | |
|---|---|
| *C07K 14/395* | (2006.01) |
| *C12N 1/16* | (2006.01) |
| *C12P 7/06* | (2006.01) |

(52) U.S. Cl.
CPC .............. *C07K 14/395* (2013.01); *C12N 1/16* (2013.01); *C12P 7/06* (2013.01)

(58) Field of Classification Search
CPC .......... C07K 14/395; C12N 1/16; C12N 9/16; C12P 7/06; C12P 7/54; Y02E 50/10
See application file for complete search history.

(56) References Cited

U.S. PATENT DOCUMENTS

| | | |
|---|---|---|
| 8,795,998 B2 | 8/2014 | Pronk et al. |
| 8,956,851 B2 | 2/2015 | Argyros et al. |
| 9,175,270 B2 | 11/2015 | Nevoigt et al. |

FOREIGN PATENT DOCUMENTS

| | | |
|---|---|---|
| WO | 2015023989 A1 | 2/2015 |
| WO | 2015148272 A1 | 10/2015 |

OTHER PUBLICATIONS

Kasavi et al., A system based network approach to ethanol tolerance in *Saccharomyces cerevisiae*. BMC Systems Biol., 2014, vol. 8:90, pp. 1-14. (Year: 2014).*

International Search Report and Written Opinion from PCT App. No. PCT/US2019/053061 dated Dec. 11, 2019, 10 pages.
Altschul et al., "Basic local alignment search tool", J Mol Biol., Oct. 1990, vol. 215, No. 3, pp. 403-410.
Altschul et al., "Local Alignment Statistics", Methods in Enzymology, vol. 266, 1996, pp. 460-480.
Cotrut, "Characterizing the Role of Gds1p in the *Saccharomyces cerevisiae* Environmental Stress Response", 2014, 114 pages.
Devereux et al., "A comprehensive set of sequence analysis programs for the VAX", Nucleic Acids Research, Jan. 1984, vol. 12, No. 1, pp. 387-395.
Duskova et al., "Two glycerol uptake systems contribute to the high osmotolerance of *Zygosaccharomyces rouxii*", Mol Microbial., vol. 97, No. 3, 2015, pp. 541-559.
Feng et al., "Progressive Sequence Alignment as a Prerequisite to Correct Phylogenetic Trees", J. Mol. Evol., vol. 25, 1987, pp. 351-360.
Ferreira et al., "A Member of the Sugar Transporter Family, Stl1p Is the Glycerol/H+ Symporter in *Saccharomyces cerevisiae*", Mol Biol Cell., vol. 16, Apr. 2005, pp. 2068-2076.
Gombert et al., "Improving conversion yield of fermentable sugars into fuel ethanol in 1st generation yeast-based production processes", Curr Opin Biotechnol., vol. 33, 2015, pp. 81-86.
Henikoff et al., "Amino acid substitution matrices from protein blocks", Proc. Natl. Acad. Sci. USA, vol. 89, Nov. 1992, pp. 10915-10919.
Higgins et al., "Fast and sensitive multiple sequence alignments on a microcomputer", Cabios Communications, vol. 5, No. 2, 1989, pp. 151-153.
Karlin et al., "Applications and statistics for multiple high-scoring segments in molecular sequences", Proc. Natl. Acad. Sci. USA, vol. 90, Jun. 1993, pp. 5873-5877.
Konopinska et al., "Nucleotide sequence of the TDS1 gene of *Saccharomyces cerevisiae*", Yeast, vol. 11, 1995, pp. 1513-1518.
Needleman et al., "A general method applicable to the search for similarities in the amino acid sequence of two proteins", J Mol Biol., Mar. 1970, vol. 48, No. 3, pp. 443-453.
Pearson et al., "Improved tools for biological sequence comparison", Proc. Natl. Acad. Sci. USA, Apr. 1988, vol. 85, No. 8, pp. 2444-2448.
Smith et al., "Comparison of biosequences", Advances in Applied Mathematics, Dec. 1981, vol. 2, Issue 4, pp. 482-489.
Sonderegger et al., "Metabolic Engineering of a Phosphoketolase Pathway for Pentose Catabolismin *Saccharomyces cerevisiae*", Appl Environ Microbial., vol. 70, No., 5, May 2004, pp. 2892-2897.
Sopko et al., "Mapping Pathways and Phenotypes by Systematic Gene Overexpression", Molecular Cell, vol. 21, No. 3, Feb. 2006, pp. 319-330.
Thompson et al., "CLUSTAL W: improving the sensitivity of progressive multiple sequence alignment through sequence weighting, position-specific gap penalties and weight matrix choice", Nucleic Acids Res., vol. 22, No. 22, 1994, pp. 4673-4680.
Wang et al.. "RNA-Seq: a revolutionary tool for transcriptomics", Nature Rev. Gen., vol. 10, 2009, pp. 57-63.
Zhang et al., "Engineering of the glycerol decomposition pathway and cofactor regulation in an industrial yeast improves ethanol production", J. Ind. Microbiol. Biotechnol., vol. 40, 2013, pp. 1153-1160.

* cited by examiner

*Primary Examiner* — Ganapathirama Raghu

(57)     ABSTRACT

Described are compositions and methods relating to modified yeast that over-express the glycerol-deficient suppressor, GDS1. The yeast produces an increased amount of ethanol and a deceased amount of acetate compared to parental cells. Such yeast is particularly useful for large-scale ethanol production from starch substrates where acetate in an undesirable end product.

12 Claims, No Drawings

Specification includes a Sequence Listing.

SEQUENCE LISTING

Sequence total quantity: 4
SEQ ID NO: 1          moltype = AA  length = 522
FEATURE               Location/Qualifiers
source                1..522
                      mol_type = protein
                      organism = Saccharomyces cerevisiae Ty1 virus
SEQUENCE: 1
MALANSRPLQ IPTLENEILH NSNSPVFQLN SMGFTTRADT ISNPGTDLIG NQPGMALDDN   60
NLAGSSFSSS QEIKATKPKK DFGAPKKDNP LLEISKLIPV TGERPKPENR DSPLDDDVLH   120
AVFLILWEMD PNQQGMTVKQ LCDLLLQKHP DMSNLSTKLS NLISAKLNAY VKKIEKGEKT   180

```
LTYALSREWS NSSPRRMLYI YRGILSPDYK EHAQAVTMQL KQQLETSGDT SDFNSNGKKK    240
RESSSNQLVN NDSYSSSMTD MKNMSSNSSF SKNLNVGNLA FSLSPEFNIP YSTSPVSLNL    300
SPSMSNNQQQ LLTPNSASKS KNNNKKRNYM DEDTNESMTE PKKTKTTKPG KQTKSQSLSV    360
LSTPKKGSSA SLSTFASSKN ISPDSSLSHN ASSNTYVTAA AAAPRLSKLL PKNGFKKNSR    420
SSSELAAIHK VISTQTPIES SSESSQYNSS SSSPVNSAAA SSAESLSDIN SSQDNGRESN    480
PSSQESRNEV TNWMKIVRNG FLTHDIESPE SITLDDLENI FN                      522
```

```
SEQ ID NO: 2             moltype = AA  length = 1569
FEATURE                  Location/Qualifiers
source                   1..1569
                         mol_type = protein
                         organism = Saccharomyces cerevisiae
SEQUENCE: 2
ATGGCATTGG CAAATTCCAG ACCTTTGCAA ATACCAACTT TAGAGAATGA AATTCTTCAT     60
AACTCAAATT CTCCAGTATT TCAGTTGAAT TCAATGGGAT TTACAACTAG AGCTGACACT    120
ATTTCGAATC CAGGCACGGA TCTTATCGGC AACCAGCCAG GCATGGCCCT TGATGATAAT    180
AATTTGGCCG GTTCTTCGTT TTCCTCATCT CAGGAAATAA AAGCTACCAA ACCTAAGGAG    240
GACTTTGGTG CTCCCAAAAA AGACAATCCA TTATTAGAAA TTTCTAAGCT AATACCTGTT    300
ACTGGTGAGA GGCCAAAACC CGAAAATAGA GACTCCCCTC TGGATGATGA CGTTCTTCAC    360
GCAGTTTTTT TAATATTATG GGAAATGGAT CCGAATCAAC AAGGCATGAC CGTCAAACAA    420
CTGTGTGACT TGCTTTTGCA AAAACATCCA GATATGTCCA ATTTATCAAC CAAGTTGTCA    480
AATTTAATTT CCGCAAAACT GAACGCTTAT GTTAAAAAAA TTGAAAAAGG TGAGAAAACG    540
TTAACTTATG CTTTATCAAG GGAATGGTCT AATTCATCTC CTAGAAGGAT GCTCTATATA    600
TACAGAGGCA TATTATCTCC CGATTACAAG GAGCATGCTC AAGCTGTTAC GATGCAACTT    660
AAACAACAAT TGGAGACCTC CGGTGATACA AGCGACTTTA ATTCAAATGG CAAGAAAAAA    720
AGGGAGTCCA GCAGTAACCA GCTAGTTAAC AATGACAGTT ATTCAAGTTC TATGACGGAC    780
ATGAAAAATA TGTCTTCTAA CAGTTCCTTC TCAAAAAATT TGAATGTAGG GAATCTGGCC    840
TTTTCATTAA GTCCAGAATT CAACATACCT TATTCCACTT CTCCAGTGTC ACTAAATCTT    900
TCCCCATCGA TGAGTAATAA TCAGCAACAA TTACTGACAC CTAATTCGGC ATCGAAGAGT    960
AAAAACAATA ATAAAAAAAG AAATTACATG GATGAAGATA CTAACGAGTC AATGACCGAG   1020
CCAAAGAAAA CCAAAACTAC TAAACCTGGC AAACAAACAA AATCCCAATC TTTATCAGTT   1080
TTATCCACCC CCAAAAAGGG TTCCTCTGCA TCTCTTTCTA CATTTGCAAG CTCCAAGAAT   1140
ATTTCGCCAG ATTCTTCTCT GTCGCATAAT GCATCGTCAA ATACTTATGT TACTGCCGCT   1200
GCCGCTGCAC AAGGCTTTC TAAGCTTTTG CCGAAAAATG GGTTTAAGAA AAATTCACGT   1260
AGCTCTTCTG AACTGGCTGC TATCCATAAA GTAATCTCTA CACAGACTCC AATTGAGAGC   1320
TCTTCAGAGA GCTCTCAATA TAACAGTAGT AGTAGTTCAC CAGTTAATAG TGCAGCTGCT   1380
TCTTCTGCTG AATCTTTATC CGACATCAAT TCCAGTCAGG ATAACGGAAG AGAATCAAAC   1440
CCAAGTTCCC AAGAATCACG AAACGAAGTT ACGAATTGGA TGAAAATTGT GAGAAATGGA   1500
TTTTTGACAC ATGATATTGA ATCTCCTGAA TCAATCACAT TAGATGACCT AGAAAATATA   1560
TTCAATTGA                                                          1569
```

```
SEQ ID NO: 3             moltype = AA  length = 899
FEATURE                  Location/Qualifiers
source                   1..899
                         mol_type = protein
                         organism = synthetic construct
SEQUENCE: 3
TCTTCAGATT CCCTCATGGA GAAAGTGCGG CAGATGTATA TGACAGAGTC GCCAGTTTCC     60
AAGAGACTTT ATTCAGGCAC TTCCATGATA GGCAAGAGAG AAGACCCAGA GATGTTGTTG    120
TCCTAGTTAC ACATGGTATT TATTCCAGAG TATTCCTGAT GAAATGGTTT AGATGGACAT    180
ACGAAGAGTT TGAATCGTTT ACCAATGTTC CTAACGGTGG CGTAATGGTG ATGGAACTGG    240
ACGAATCCAT CAATAGATAC GTCCTGAGGA CCGTGCTACC CAAATGGACT GATTGTGAGG    300
GAGACCTAAC TACATAGTGT TTAAAGATTA CGGATATTTA ACTTACTTAG AATAATGCCA    360
TTTTTTTTGAG TTATAATAAT CCTACGTTAG TGTGAGCGGG ATTTAAACTG TGAGGACCTT    420
AATACATTCA GACACTTCTG CGGTATCACC CTACTTATTC CCTTCGAGAT TATATCTAGG    480
AACCCATCAG GTTGGTGGAA GATTACCCGT TCTAAGACTT TTCAGCTTCC TCTATTGATG    540
TTACACCTGG ACACCCCTTT TCTGGCATCC AGTTTTTAAT CTTCAGTGGC ATGTGAGATT    600
CTCCGAAATT AATTAAAGCA ATCACACAAT TCTCTCGGAT ACCACCTCGG TTGAAACTGA    660
CAGGTGGTTT GTTACGCATG CTAATGCAAA GGAGCCTATA TACCTTTGGC TCGGCTGCTG    720
TAACAGGGAA TATAAAGGGC AGCATAATTT AGGAGTTTAG TGAACTTGCA ACATTTACTA    780
TTTTCCCTTC TTACGTAAAT ATTTTTCTTT TTAATTCTAA ATCAATCTTT TTCAATTTTT    840
TGTTTGTATT CTTTTCTTGC TTAAATCTAT AACTACAAAA AACACATACA TAAACTAAA     899
```

```
SEQ ID NO: 4             moltype = AA  length = 300
FEATURE                  Location/Qualifiers
source                   1..300
                         mol_type = protein
                         organism = synthetic construct
SEQUENCE: 4
TTTTTATCTC CCTTTACAAG AGCATAACGG CTGCTCTACA CCTATGTCGT TGTTTTTTTT     60
TTTTCAACTA ATAATATGTG TTCCTCTCAT TTGGACAATT TTTAGCTAGT TCTAACTTTC    120
ACTACAATAT TTAAATAAAT AAACAACCAT AAATAAATAA ATGAAAAACA ATTAAACCGT    180
TAGAGGTGGA CTAATTTACT GTTAATGACA GTAATTTTTT TTTTTTTGGC TGTTTTCGGT    240
TATTCCGGAT ATATATGGAT TGATCTTCAT TTACCCCACA GTTAGTTTAT CCGAAATTTA    300
```

OVER-EXPRESSION OF GDS1 IN YEAST FOR INCREASED ETHANOL AND DECREASED ACETATE PRODUCTION

CROSS REFERENCE

The present application is a Continuation of U.S. application Ser. No. 17/281,068, filed Mar. 29, 2021, which is a 371 of International Application No. PCT/US19/053061, filed Sep. 26, 2019 and claims the benefit of U.S. Provisional Application Ser. No. 62/738,582, filed Sep. 28, 2018, all of which are hereby incorporated by reference in their entirety.

INCORPORATION BY REFERENCE OF THE SEQUENCE LISTING

The present application is being filed along with a Sequence Listing in electronic format. The Sequence Listing is provided as a file entitled NB41572USPCN_SequenceListing.xml, created Jun. 6, 2023, which is 8 KB in size. The information in the electronic format of the Sequence Listing is incorporated by reference in its entirety.

TECHNICAL FIELD

The present compositions and methods relate to modified yeast that over-expresses the glycerol-deficient suppressor, GDS1. The yeast produces an increased amount of ethanol and a deceased amount of acetate compared to parental cells. Such yeast is particularly useful for large-scale ethanol production from starch substrates, where acetate in an undesirable by-product.

BACKGROUND

First-generation yeast-based ethanol production converts sugars into fuel ethanol. The annual fuel ethanol production by yeast is about 90 billion liters worldwide (Gombert, A. K. and van Maris. A. J. (2015) *Curr. Opin. Biotechnol.* 33:81-86). It is estimated that about 70% of the cost of ethanol production is the feedstock. Since the production volume is so large, even small yield improvements have massive economic impact across the industry.

The phosphoketolase (PKL) pathway has been genetically engineered into yeast to increase ethanol production, as described in WO2015148272 (Miasnikov et al.). Unfortunately, the engineered strains also produce more acetate than the parental yeast. Acetate is not a desirable by-product as it has negative effects on yeast growth and fermentation. In addition, acetate reduces the pH of left-over water from fermentation and distillation, referred to as backset, which is typically reused for liquefaction of a subsequent batch of substrate. As a result, ethanol producers must adjust the pH of the backset (or liquefact) or increase the amount of fresh water used for liquefaction.

The need exists to control the amount of acetate produced by yeast, particularly engineered yeast that tend to produce an increased amount of acetate.

SUMMARY

The present compositions and methods relate to modified yeast that over-express GDS1 polypeptides. Aspects and embodiments of the compositions and methods are described in the following, independently-numbered, paragraphs.

1. In one aspect, modified yeast cells derived from parental yeast cells are provided, the modified cells comprising a genetic alteration that causes the modified cells to produce an increased amount of GDS1 polypeptides compared to the parental cells, wherein the modified cells produce during fermentation a decreased amount of acetate compared to the amount of acetate produced by the parental cells under identical fermentation conditions.

2. In some embodiments of the modified yeast cells of paragraph 1, the modified cells produce during fermentation an increased amount of ethanol compared to the amount of ethanol produced by the parental cells under identical fermentation conditions.

3. In some embodiments of the modified cells of paragraph 1 or 2, the genetic alteration comprises the introduction into the parental cells of a nucleic acid capable of directing the expression of a GDS1 polypeptide to a level above that of the parental cell grown under equivalent conditions.

4. In some embodiments of the modified cells of paragraph 1 or 2, the genetic alteration comprises the introduction of an expression cassette for expressing a GDS1 polypeptide.

5. In some embodiments of the modified cells of any of paragraphs 1-5, the cells further comprising one or more genes of the phosphoketolase pathway.

6. In some embodiments of the modified cells of paragraph 5, the genes of the phosphoketolase pathway are selected from the group consisting of phosphoketolase, phosphotransacetylase and acetylating acetyl dehydrogenase.

7. In some embodiments of the modified cells of any of paragraphs 1-6, the amount of increase in the expression of the GDS1 polypeptide is at least about 500% compared to the level expression in the parental cells grown under equivalent conditions.

8. In some embodiments of the modified cells of any of paragraphs 1-6, the amount of increase in the production of mRNA encoding the GDS1 polypeptide is at least about 1000% compared to the level in the parental cells grown under equivalent conditions.

9. In some embodiments of the modified cells of any of paragraphs 1-6, the amount of increase in the production of mRNA encoding the GDS1 polypeptide is at least about 5000% compared to the level in the parental cells grown under equivalent conditions.

10. In some embodiments of the modified cells of any of paragraphs 1-6, the amount of increase in the production of mRNA encoding the GDS1 polypeptide is at least about 10000% compared to the level in the parental cells grown under equivalent conditions.

11. In some embodiments of the modified cells of any of paragraphs 1-10, the cells further comprise an exogenous gene encoding a carbohydrate processing enzyme.

12. In some embodiments, the modified cells of any of paragraphs 1-11 further comprise an alteration in the glycerol pathway and/or the acetyl-CoA pathway.

13. In some embodiments, the modified cells of any of paragraphs 1-12 further comprise an alternative pathway for making ethanol.

14. In some embodiments of the modified cells of any of paragraphs 1-13, the cells are of a *Saccharomyces* spp.

15. In another aspect, a method for decreasing the production of acetate from yeast cells grown on a carbohydrate substrate is provided, comprising: introducing into parental yeast cells a genetic alteration that increases the production of GDS1 polypeptides compared to the amount produced in the parental cells.

16. In another aspect, a method for increasing the production of ethanol from yeast cells grown on a carbohydrate substrate is provided, comprising: introducing into parental yeast cells a genetic alteration that increases the production of GDS1 polypeptides compared to the amount produced in the parental cells.

17. In some embodiments of the method of paragraph 15 or 16, the cells having the introduced genetic alteration are the modified cells are the cells of any of paragraphs 1-15.

18. In some embodiments of the method of paragraph 15 or 17, the decrease in acetate production is at least 10%, at least 15%, at least 20%, or at least 25%, or at least 30% compared to the amount produced in the parental cells.

19. In some embodiments of the method of paragraph 16 or 17, the increase in ethanol production is at least 0.1%, at least 0.2%, at least 0.3%, or at least 0.5%, or at least 1.0% compared to the amount produced in the parental cells.

20. In some embodiments of the method of any of paragraphs 15-19, GDS1 polypeptides are over-expressed by at least 500%.

21. In some embodiments of the method of any of paragraphs 15-19, GDS1 polypeptides are over-expressed by at least 5-fold.

22. In some embodiments of the method of any of paragraphs 15-19, GDS1 polypeptides are over-expressed by at least 10-fold.

23. In some embodiments of the method of any of paragraphs 15-19, GDS1 polypeptides are over-expressed by at least 50-fold.

24. In some embodiments of the method of any of paragraphs 15-19, GDS1 polypeptides are over-expressed by at least 100-fold.

These and other aspects and embodiments of present modified cells and methods will be apparent from the description, including any accompanying Drawings/Figures.

DETAILED DESCRIPTION

I. Definitions

Prior to describing the present yeast and methods in detail, the following terms are defined for clarity. Terms not defined should be accorded their ordinary meanings as used in the relevant art.

As used herein, the term "alcohol" refers to an organic compound in which a hydroxyl functional group (—OH) is bound to a saturated carbon atom.

As used herein, the terms "yeast cells," "yeast strains," or simply "yeast" refer to organisms from the phyla Ascomycota and Basidiomycota. Exemplary yeast is budding yeast from the order Saccharomycesles. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "engineered yeast cells," "variant yeast cells," "modified yeast cells," or similar phrases, refer to yeast that include genetic modifications and characteristics described herein. Variant/modified yeast do not include naturally occurring yeast.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins," or "homologs." Such proteins can be derived from organisms of different genera and/or species, or different classes of organisms (e.g., bacteria and fungi), or artificially designed. Related proteins also encompass homologs determined by primary sequence analysis, determined by secondary or tertiary structure analysis, or determined by immunological cross-reactivity, or determined by their functions.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.*

266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF |

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype. The term "allele" is generally preferred when an organism contains more than one similar genes, in which case each different similar gene is referred to as a distinct "allele."

As used herein, "constitutive" expression refers to the production of a polypeptide encoded by a particular gene under essentially all typical growth conditions, as opposed to "conditional" expression, which requires the presence of a particular substrate, temperature, or the like to induce or activate expression.

As used herein, the term "expressing a polypeptide" and similar terms refers to the cellular process of producing a polypeptide using the translation machinery (e.g., ribosomes) of the cell.

As used herein, "over-expressing a polypeptide," "increasing the expression of a polypeptide," and similar terms, refer to expressing a polypeptide at higher-than-normal levels compared to those observed with parental or "wild-type cells that do not include a specified genetic modification.

As used herein, an "expression cassette" refers to a DNA fragment that includes a promoter, and amino acid coding region and a terminator (i.e., promoter::amino acid coding region::terminator) and other nucleic acid sequence needed to allow the encoded polypeptide to be produced in a cell. Expression cassettes can be exogenous (i.e., introduced into a cell) or endogenous (i.e., extant in a cell).

As used herein, the terms "fused" and "fusion" with respect to two DNA fragments, such as a promoter and the coding region of a polypeptide refer to a physical linkage causing the two DNA fragments to become a single molecule.

As used herein, the terms "wild-type" and "native" are used interchangeably and refer to genes, proteins or strains found in nature, or that are not intentionally modified for the advantage of the presently described yeast.

As used herein, the term "protein of interest" refers to a polypeptide that is desired to be expressed in modified yeast. Such a protein can be an enzyme, a substrate-binding protein, a surface-active protein, a structural protein, a selectable marker, a signal transducer, a receptor, a transporter, a transcription factor, a translation factor, a co-factor, or the like, and can be expressed. The protein of interest is encoded by an endogenous gene or a heterologous gene (i.e., gene of interest") relative to the parental strain. The protein of interest can be expressed intracellularly or as a secreted protein.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using CRISPR, RNAi, antisense, or any other method that abolishes gene expression. A gene can be disrupted by deletion or genetic manipulation of non-adjacent control elements. As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements. Deletion of a gene also refers to the deletion a part of the coding sequence, or a part of promoter immediately or not immediately adjacent to the coding sequence, where there is no functional activity of the interested gene existed in the engineered cell.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "functional polypeptide/protein" is a protein that possesses an activity, such as an enzymatic activity, a binding activity, a surface-active property, a signal transducer, a receptor, a transporter, a transcription factor, a translation factor, a co-factor, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "attenuation of a pathway" or "attenuation of the flux through a pathway," i.e., a biochemical pathway, refers broadly to any genetic or chemical manipulation that reduces or completely stops the flux of biochemical substrates or intermediates through a metabolic pathway. Attenuation of a pathway may be achieved by a variety of well-known methods. Such methods include but are not limited to: complete or partial deletion of one or more genes, replacing wild-type alleles of these genes with mutant forms encoding enzymes with reduced catalytic activity or increased Km values, modifying the promoters or other regulatory elements that control the expression of one or more genes, engineering the enzymes or the mRNA encoding these enzymes for a decreased stability, misdirecting enzymes to cellular compartments where they are less likely to interact with substrate and intermediates, the use of interfering RNA, and the like.

As used herein, "aerobic fermentation" refers to growth in the presence of oxygen.

As used herein, "anaerobic fermentation" refers to growth in the absence of oxygen.

As used herein, the expression "end of fermentation" refers to the stage of fermentation when the economic advantage of continuing fermentation to produce a small amount of additional alcohol is exceeded by the cost of continuing fermentation in terms of fixed and variable costs. In a more general sense, "end of fermentation" refers to the point where a fermentation will no longer produce a significant amount of additional alcohol, i.e., no more than about 1% additional alcohol, or no more substrate left for further alcohol production.

As used herein, the expression "carbon flux" refers to the rate of turnover of carbon molecules through a metabolic pathway. Carbon flux is regulated by enzymes involved in metabolic pathways, such as the pathway for glucose metabolism and the pathway for maltose metabolism.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

| EC | enzyme commission |
|---|---|
| PKL | phosphoketolase |
| PTA | phosphotransacetylase |
| AADH | acetaldehyde dehydrogenases |
| ADH | alcohol dehydrogenase |
| EtOH | ethanol |
| GDS1 | glycerol-deficient suppressor |
| AA | α-amylase |
| GA | glucoamylase |
| ° C. | degrees Centigrade |
| bp | base pairs |
| DNA | deoxyribonucleic acid |
| ds or DS | dry solids |
| g or gm | gram |
| g/L | grams per liter |
| $H_2O$ | water |
| HPLC | high performance liquid chromatography |
| hr or h | hour |
| kg | kilogram |
| M | molar |
| mg | milligram |
| mL or ml | milliliter |
| min | minute |
| mM | millimolar |
| N | normal |
| nm | nanometer |
| PCR | polymerase chain reaction |
| ppm | parts per million |
| Δ | relating to a deletion |
| μg | microgram |
| μL and μl | microliter |
| μM | micromolar |

II. Modified Yeast Cells Having Increased GDS1 Expression

Described are modified yeast and methods having a genetic alteration that results in the production of increased amounts of GDS1 polypeptides compared to corresponding (i.e., otherwise-identical) parental cells. GDS1 is a 522-amino acid residue, serine-rich polypeptide identified as a suppressor of certain glycerol-deficient phenotypes. GDS1 appears to have no obvious homology to other know yeast proteins (see, e.g., Konopinska, A. et al. (1995) Yeast 11:1513-18). GDS1 is important for yeast cells to grow on medium containing glycerol as the carbon source. However, no association has been made between GDS1 over-expression and acetate reduction and/or ethanol increase in engineered yeast.

Applicants have discovered that yeast cells over-expressing GDS1 polypeptides produce a decreased amount of acetate and an increased amount of ethanol compared to otherwise-identical parental cells. Decreased acetate is desirable as acetate adversely affects yeast growth and fermentation and additionally results in backset that has a lower than desirable pH, requiring pH adjustment or the use of more fresh water to dilute the backset.

In some embodiments, the increase in the amount of GDS1 polypeptides produced by the modified cells is an increase of at least 1000%, at least 2500%, at least 5000%, at least at least 10000%, or more, especially at early stage of fermentation, compared to the amount of GDS1 polypeptides produced by parental cells grown under the same conditions.

In some embodiments, the increase in the amount of GDS1 polypeptides produced by the modified cells is at least 10-fold, at least 25-fold, at least 50-fold, at least 100-fold, or more, compared to the amount of GDS1 polypeptides produced by parental cells grown under the same conditions.

In some embodiments, the increase in the strength of the promoter used to control expression of the GDS1 polypeptides produced by the modified cells is at least 10-fold, at least 25-fold, at least 50-fold, at least 100-fold, or more, compared to strength of the native promoter controlling GDS1 expression, based on the amount of mRNA produced. As shown in Table 1, RNAseq data (see, e.g., Wang, Z. et al. (2009) *Nature Rev. Gen.* 10:57-63) indicates that the TPI1 promoter used for the exemplified GDS1 expression cassette is at least 76-times stronger than the normal native GDS1 promoter during early-stage fermentation in the parental FERMAX™ Gold strain (Martrex Inc., Minnesota, USA; herein abbreviated, "FG," a well-known commercially-available fermentation yeast used in the grain ethanol industry).

TABLE 1

| RNAseq analyses of GDS1 and TPI1 in the FG strain | | | |
|---|---|---|---|
| Promoter | 0 hr | 6 hr | 24 hr |
| native GDS1 | 764 | 965 | 89 |
| RHO1 | 58337 | 98377 | 23003 |

In some embodiments, the decrease in acetate production by the modified cells is a decrease of at least 10%, at least 15%, at least 20%, at least 25%, at least 30%, at least 35%, at least 40%, or at least 50%, more, compared to the amount of acetate produced by parental cells grown under the same conditions.

In some embodiments, the increase in ethanol production by the modified cells is an increase of at least 0.1%, at least 0.3%, or at least 0.5%, or at least 1%, or more, compared to the amount of ethanol produced by parental cells grown under the same conditions.

Preferably, increased GDS1 expression is achieved by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the present compositions and methods involve introducing into yeast cells a nucleic acid capable of directing the over-expression, or increased expression, of a GDS1 polypeptide. Particular methods include but are not limited to (i) introducing an exogenous expression cassette for producing the polypeptide into a host cell, optionally in addition to an endogenous expression cassette, (ii) substituting an exogenous expression cassette with an endogenous cassette that allows the production of an increased amount of the polypeptide, (iii) modifying the promoter of an endogenous expression cassette to increase expression, (iv) increase copy number of the same or different cassettes for over-expression of GDS1, and/or (v) modifying any aspect of the host cell to increase the half-life of the polypeptide in the host cell.

In some embodiments, the parental cell that is modified already includes a gene of interest, such as a gene encoding a selectable marker, carbohydrate-processing enzyme, or other polypeptide. In some embodiments, a gene of introduced is subsequently introduced into the modified cells.

In some embodiments, the parental cell that is modified already includes an engineered pathway of interest, such as a PKL pathway to increases ethanol production, or any other pathway to increase alcohol production.

The amino acid sequence of the exemplified *S. cerevisiae* GDS1 polypeptide is shown, below, as SEQ ID NO: 1:

```
MALANSRPLQIPTLENEILHNSNSPVFQLNSMGFTTRADTISNPGTDLI

GNQPGMALDDNNLAGSSFSSSQEIKATKPKKDFGAPKKDNPLLEISKLI

PVTGERPKPENRDSPLDDDVLHAVFLILWEMDPNQQGMTVKQLCDLLLQ

KHPDMSNLSTKLSNLISAKLNAYVKKIEKGEKTLTYALSREWSNSSPRR

MLYIYRGILSPDYKEHAQAVTMQLKQQLETSGDTSDFNSNGKKKRESSS

NQLVNNDSYSSSMTDMKNMSSNSSFSKNLNVGNLAFSLSPEFNIPYSTS

PVSLNLSPSMSNNQQQLLTPNSASKSKNNNKKRNYMDEDTNESMTEPKK

TKTTKPGKQTKSQSLSVLSTPKKGSSASLSTFASSKNISPDSSLSHNAS

SNTYVTAAAAPRLSKLLPKNGFKKNSRSSSELAAIHKVISTQTPIESS

SESSQYNSSSSSPVNSAAASSAESLSDINSSQDNGRESNPSSQESRNEV

TNWMKIVRNGFLTHDIESPESITLDDLENIFN
```

The NCBI database includes over 100 entries for *S. cerevisiae* GDS1 polypeptides. Natural variations in the amino acid sequence are not expected to affect its function. In addition, based on such BLAST and Clustal W data, it is apparent that the exemplified *S. cerevisiae* GDS1 polypeptide shares a high degree of sequence identity to polypeptides from other organisms, and over-expression of functionally and/or structurally similar proteins, homologous proteins and/or substantially similar or identical proteins, is expected to produce similar beneficial results.

In particular embodiments of the present compositions and methods, the amino acid sequence of the GDS1 polypeptide that is over-expressed in modified yeast cells has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1.

III. Modified Yeast Cells Having Increased GDS1 Expression in Combination with Genes of an Exogenous PKL Pathway Increased expression of GDS1 can be combined with expression of genes in the PKL pathway to further increase ethanol production and reduce the production of elevated amounts of acetate that is associated with introducing an exogenous PKL pathway into yeast.

Engineered yeast cells having a heterologous PKL pathway have been previously described in WO2015148272 (Miasnikov et al.). These cells express heterologous phosphoketolase (PKL), phosphotransacetylase (PTA) and acetylating acetyl dehydrogenase (AADH), optionally with other enzymes, to channel carbon flux away from the glycerol pathway and toward the synthesis of acetyl-CoA, which is then converted to ethanol. Such modified cells are capable of increased ethanol production in a fermentation process when compared to otherwise-identical parent yeast cells.

IV. Combination of Increased Active GDS1 Production with Other Mutations that Alter Alcohol or Acetate Production In some embodiments, in addition to expressing increased amounts of active GDS1 polypeptides, optionally in combination with introducing an exogenous PKL pathway, the present modified yeast cells include additional modifications that increase ethanol or reduce acetate production.

The modified cells may further include mutations that result in attenuation of the native glycerol biosynthesis pathway and/or reuse glycerol pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.). Methods to enhance the reuse glycerol pathway by over expression of glycerol dehydrogenase (GCY1) and dihydroxyacetone kinase (DAK1) to convert glycerol to dihydroxyacetone phosphate (Zhang et al; *J Ind Microbiol Biotechnol* (2013) 40:1153-1160).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-COA. This partially reduces the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like.

In some embodiments the modified cells may further include a heterologous gene encoding a protein with NAD$^+$-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.). In some embodiments of the present compositions and methods the yeast expressly lacks a heterologous gene(s) encoding an acetylating acetaldehyde dehydrogenase, a pyruvate-formate lyase or both.

In some embodiments, the present modified yeast cells may further over-express a sugar transporter-like (STL1) polypeptide to increase the uptake of glycerol (see, e.g., Ferreira et al. (2005) *Mol. Biol. Cell.* 16:2068-76; Dušková et al. (2015) *Mol. Microbiol.* 97:541-59 and WO 2015023989 A1) to increase ethanol production and reduce acetate.

In some embodiments, the present modified yeast cells further include a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

V. Combination of Increased Expression GDS1 with Other Beneficial Mutations

In some embodiments, in addition to increased expression of GDS1 polypeptides, optionally in combination with other genetic modifications that benefit alcohol production, the present modified yeast cells further include any number of additional genes of interest encoding proteins of interest. Additional genes of interest may be introduced before, during, or after genetic manipulations that result in the increased production of GDS1 polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transladolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Use of the Modified Yeast for Increased Alcohol Production

The present compositions and methods include methods for increasing alcohol production and/or reducing glycerol production, in fermentation reactions. Such methods are not limited to a particular fermentation process. The present engineered yeast is expected to be a "drop-in" replacement for convention yeast in any alcohol fermentation facility. While primarily intended for fuel alcohol production, the present yeast can also be used for the production of potable alcohol, including wine and beer.

VII. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces*, Lachancea and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VII. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present yeast strains and methods will be apparent to the skilled person in view of the present description. The following examples are intended to further illustrate, but not limit, the compositions and methods.

EXAMPLES

Example 1

Materials and Methods

Liquefact Preparation:

Liquefact (corn mash slurry) was prepared by adding 600 ppm of urea, 0.124 SAPU/g ds acid fungal protease, 0.33 GAU/g ds variant *Trichoderma* glucoamylase and 1.46 SSCU/g ds *Aspergillus kawachii* α-amylase, adjusted to a pH of 4.8 with sulfuric acid.

AnKom Assays:

300 µL of concentrated yeast overnight culture was added to each of a number ANKOM bottles filled with 50 g prepared liquefact (see above) to a final OD of 0.3. The bottles were then incubated at 32° C. with shaking at 150 RPM for 55 hours.

HPLC Analysis:

Samples of the cultures from AnKom assays were collected in Eppendorf tubes by centrifugation for 12 minutes at 14,000 RPM. The supernatants were filtered using 0.2 µM PTFE filters and then used for HPLC (Agilent Technologies 1200 series) analysis with the following conditions: Bio-Rad Aminex HPX-87H columns, running at a temperature of 55° C. with a 0.6 ml/min isocratic flow in 0.01 N H2SO4 and a 2.5 µl injection volume. Calibration standards were used for quantification of the of acetate, ethanol, glycerol, glucose and other molecules. Unless otherwise indicated, all values are reported in g/L.

Example 2

Preparation of a GDS1 Expression Cassette

The GDS1 coding region at the YOR355W locus (SEQ ID NO:2) of *S. cerevisiae* was synthesized and operably linked to the TPI1 promoter (YDR050C locus; SEQ ID NO: 3) and GDS1 terminator (YOR355W locus; SEQ ID NO: 4) to generate the TPI1Pro::GDS1s::Gds1Ter expression cassette, referred to herein as GDS1s. The expression cassette was introduced between positions 476541 and 476599 of yeast chromosome IV either (i) FERMAX™ Gold (Martrex Inc., Minnesota, USA; herein abbreviated, "FG"), which is a well-known fermentation yeast used in the grain ethanol industry, or (ii) FG-PKR, which is an engineered FG yeast having a heterologous phosphoketolase (PKL) pathway involving the expression of phosphoketolase (PKL), phosphotransacetylase (PTA) and acetylating acetyl dehydrogenase (AADH) as described in WO2015148272 (Miasnikov et al.). The expected insertion of the GDS1s expression cassette in the two parental strains was confirmed by PCR analyses.

The amino acid sequence of the *S. cerevisiae* GDS1 polypeptide is shown, below, as SEQ ID NO: 1:

```
MALANSRPLQIPTLENEILHNSNSPVFQLNSMGFTTRADTISNPGTDLI

GNQPGMALDDNNLAGSSFSSSQEIKATKPKKDFGAPKKDNPLLEISKLI

PVTGERPKPENRDSPLDDDVLHAVFLILWEMDPNQQGMTVKQLCDLLLQ

KHPDMSNLSTKLSNLISAKLNAYVKKIEKGEKTLTYALSREWSNSSPRR

MLYIYRGILSPDYKEHAQAVTMQLKQQLETSGDTSDFNSNGKKKRESSS

NQLVNNDSYSSSMTDMKNMSSNSSFSKNLNVGNLAFSLSPEFNIPYSTS

PVSLNLSPSMSNNQQQLLTPNSASKSKNNNKKRNYMDEDINESMTEPKK

TKTTKPGKQTKSQSLSVLSTPKKGSSASLSTFASSKNISPDSSLSHNAS

SNTYVTAAAAAPRLSKLLPKNGFKKNSRSSSELAAIHKVISTQTPIESS

SESSQYNSSSSSPVNSAAASSAESLSDINSSQDNGRESNPSSQESRNEV

TNWMKIVRNGFLTHDIESPESITLDDLENIFN
```

The GDS1-coding region of the GDS1s gene is shown, below, as SEQ ID NO: 2:

```
ATGGCATTGGCAAATTCCAGACCTTTGCAAATACCAACTTTAGAGAATG

AAATTCTTCATAACTCAAATTCTCCAGTATTTCAGTTGAATTCAATGGG

ATTTACAACTAGAGCTGACACTATTTCGAATCCAGGCACGGATCTTATC

GGCAACCAGCCAGGCATGGCCCTTGATGATAATAATTTGGCCGGTTCTT

CGTTTTCCTCATCTCAGGAAATAAAAGCTACCAAACCTAAGAAGGACTT

TGGTGCTCCCAAAAAAGACAATCCATTATTAGAAATTTCTAAGCTAATA

CCTGTTACTGGTGAGAGGCCAAAACCCGAAAATAGAGACTCCCCTCTGG

ATGATGACGTTCTTCACGCAGTTTTTTTAATATTATGGGAAATGGATCC

GAATCAACAAGGCATGACCGTCAAACAACTGTGTGACTTGCTTTTGCAA

AAACATCCAGATATGTCCAATTTATCAACCAAGTTGTCAAATTTAATTT

CCGCAAAACTGAACGCTTATGTTAAAAAAATTGAAAAAGGTGAGAAAAC

GTTAACTTATGCTTTATCAAGGGAATGGTCTAATTCATCTCCTAGAAGG

ATGCTCTATATATACAGAGGCATATTATCTCCCGATTACAAGGAGCATG

CTCAAGCTGTTACGATGCAACTTAAACAACAATTGGAGACCTCCGGTGA

TACAAGCGACTTTAATTCAAATGGCAAGAAAAAAAGGGAGTCCAGCAGT

AACCAGCTAGTTAACAATGACAGTTATTCAAGTTCTATGACGGACATGA

AAAATATGTCTTCTAACAGTTCCTTCTCAAAAAATTTGAATGTAGGGAA

TCTGGCCTTTTCATTAAGTCCAGAATTCAACATACCTTATTCCACTTCT

CCAGTGTCACTAAATCTTTCCCCATCGATGAGTAATAATCAGCAACAAT

TACTGACACCTAATTCGGCATCGAAGAGTAAAAACAATAATAAAAAAAG

AAATTACATGGATGAAGATACTAACGAGTCAATGACCGAGCCAAAGAAA

ACCAAAACTACTAAACCTGGCAAACAAACAAAATCCCAATCTTTATCAG

TTTTATCCACCCCCAAAAAGGGTTCCTCTGCATCTCTTTCTACATTTGC

AAGCTCCAAGAATATTTCGCCAGATTCTTCTCTGTCGCATAATGCATCG
```

-continued

TCAAATACTTATGTTACTGCCGCTGCCGCTGCACCAAGGCTTTCTAAGC

TTTTGCCGAAAAATGGGTTTAAGAAAAATTCACGTAGCTCTTCTGAACT

GGCTGCTATCCATAAAGTAATCTCTACACAGACTCCAATTGAGAGCTCT

TCAGAGAGCTCTCAATATAACAGTAGTAGTAGTTCACCAGTTAATAGTG

CAGCTGCTTCTTCTGCTGAATCTTTATCCGACATCAATTCCAGTCAGGA

TAACGGAAGAGAATCAAACCCAAGTTCCCAAGAATCACGAAACGAAGTT

ACGAATTGGATGAAAATTGTGAGAAATGGATTTTTGACACATGATATTG

AATCTCCTGAATCAATCACATTAGATGACCTAGAAAATATATTCAATTG

A

The TPI1 promoter region used for GDS1s over-expression shown, below, as SEQ ID NO: 3:

TCTTCAGATTCCCTCATGGAGAAAGTGCGGCAGATGTATATGACAGAGT

CGCCAGTTTCCAAGAGACTTTATTCAGGCACTTCCATGATAGGCAAGAG

AGAAGACCCAGAGATGTTGTTGTCCTAGTTACACATGGTATTTATTCCA

GAGTATTCCTGATGAAATGGTTTAGATGGACATACGAAGAGTTTGAATC

GTTTACCAATGTTCCTAACGGGAGCGTAATGGTGATGGAACTGGACGAA

TCCATCAATAGATACGTCCTGAGGACCGTGCTACCCAAATGGACTGATT

GTGAGGGAGACCTAACTACATAGTGTTTAAAGATTACGGATATTTAACT

TACTTAGAATAATGCCATTTTTTTGAGTTATAATAATCCTACGTTAGTG

TGAGCGGGATTTAAACTGTGAGGACCTTAATACATTCAGACACTTCTGC

GGTATCACCCTACTTATTCCCTTCGAGATTATATCTAGGAACCCATCAG

GTTGGTGGAAGATTACCCGTTCTAAGACTTTTCAGCTTCCTCTATTGAT

GTTACACCTGGACACCCCTTTTCTGGCATCCAGTTTTTAATCTTCAGTG

GCATGTGAGATTCTCCGAAATTAATTAAAGCAATCACACAATTCTCTCG

GATACCACCTCGGTTGAAACTGACAGGTGGTTTGTTACGCATGCTAATG

CAAAGGAGCCTATATACCTTTGGCTCGGCTGCTGTAACAGGGAATATAA

AGGGCAGCATAATTTAGGAGTTTAGTGAACTTGCAACATTTACTATTTT

CCCTTCTTACGTAAATATTTTTCTTTTTAATTCTAAATCAATCTTTTTC

AATTTTTTGTTTGTATTCTTTTCTTGCTTAAATCTATAACTACAAAAAA

CACATACATAAACTAAA

The TGDS1 terminator region used for GDS1s over-expression shown, below, as SEQ ID NO: 4:

TTTTTATCTCCCTTTACAAGAGCATAACGGCTGCTCTACACCTATGTCG

TTGTTTTTTTTTTTTCAACTAATAATATGTGTTCCTCTCATTTGGACAA

TTTTTAGCTAGTTCTAACTTTCACTACAATATTTAAATAAATAAACAAC

CATAAATAAATAAATGAAAAACAATTAAACCGTTAGAGGTGGACTAATT

TACTGTTAATGACAGTAATTTTTTTTTTTTTTGGCTGTTTTCGGTTATTC

CGGATATATATGGATTGATCTTCATTTACCCCACAGTTAGTTTATCCGA

AATTTA

Example 3

Alcohol Production Using Yeast that Over-Express GDS1

Strains over-expressing GDS1 were tested in an Ankom assay, containing 50 g liquefact, as described in Example 1. Fermentations were performed at 32° C. for 55 hours. Samples from the end of fermentation were analyzed by HPLC. The results are summarized in Tables 2 and 3.

TABLE 2

| HPLC results with strains FG and FG-TS using an Ankom assay | | | | |
| --- | --- | --- | --- | --- |
| Strain | Glycerol (g/L) | Acetate (g/L) | Ethanol (g/L) | EtOH increase (%) | Acetate reduction (%) |
| FG | 14.7 | 0.74 | 137.7 | -0- | -0- |
| FG-TS | 14.8 | 0.53 | 138.2 | 0.3% | 28.4% |

TABLE 3

| HPLC results with strains FG-PKL and FG-PKL-TS using an Ankom assay | | | | |
| --- | --- | --- | --- | --- |
| Strain | Glycerol (g/L) | Acetate (g/L) | Ethanol (g/L) | EtOH increase (%) | Acetate reduction (%) |
| FG-PKL | 12.1 | 1.31 | 144.0 | -0- | -0- |
| FG-PKL-TS | 11.9 | 1.09 | 144.7 | 0.5% | 16.8% |

Over-expression of GDS1 resulted in a decrease of acetate production of about 28% in FG yeast, which is recognized as a robust, non-genetically-engineered, high-ethanol-producing yeast for the fuel ethanol industry. Over-expression of GDS1 resulted in a decrease of acetate production by of about 16.8% in FG yeast engineered to have an exogenous PKL pathway. Furthermore, over-expression GDS1 resulted in an increase of 0.3% and 0.5% in ethanol production in FG and FG-PKL, respectively. These results demonstrate that GDS1 over-expression is beneficial for reducing acetate, and increasing ethanol production in engineered yeast strains.

What is claimed is:

1. A method for increasing the production of ethanol from yeast cells grown on a carbohydrate substrate, comprising: introducing into parental yeast cells a genetic alteration that increases the production of glycerol-deficient suppressor (GDS1) polypeptides compared to the amount produced in the parental cells;

wherein the GDS1 polypeptides comprise an amino acid sequence having at least 80% sequence identity to the amino acid sequence set forth by SEQ ID NO: 1; and wherein the yeast cells are of a *Saccharomyces* spp.

2. The method of claim 1, wherein the increase in ethanol production is at least 0.1% compared to the amount produced in the parental cells.

3. The method of claim 1, wherein GDS1 polypeptides are over-expressed by at least 500%.

4. The method of claim 1, wherein GDS1 polypeptides are over-expressed by at least 5-fold.

5. The method of claim 1, wherein the cells having the introduced genetic alteration produce during fermentation a decreased amount of acetate compared to the amount of acetate produced by the parental cells under identical fermentation conditions.

6. The method of claim 5, wherein the decrease in acetate production is at least 10% compared to the amount produced by the parental cells.

7. The method of claim 1, wherein the genetic alteration comprises introducing an expression cassette for expressing a GDS1 polypeptide.

8. The method of claim 1, wherein the cells having the introduced genetic alteration further comprise one or more genes of the phosphoketolase pathway.

9. The method of claim 8, wherein the genes of the phosphoketolase pathway are selected from the group consisting of phosphoketolase, phosphotransacetylase and acetylating acetyl dehydrogenase.

10. The method of claim 1, wherein the cells having the introduced genetic alteration further comprise an exogenous gene encoding a carbohydrate processing enzyme.

11. The method of claim 1, wherein the cells having the introduced genetic alteration further comprise an alteration in the glycerol pathway and/or the acetyl-CoA pathway.

12. The method of claim 1, wherein the cells having the introduced genetic alteration further comprise an alternative pathway for making ethanol.

* * * * *